(12) United States Patent
Lee et al.

(10) Patent No.: US 9,539,226 B2
(45) Date of Patent: Jan. 10, 2017

(54) COMPOSITION CONTAINING SERINE AS AN ACTIVE INGREDIENT FOR THE PREVENTION AND TREATMENT OF FATTY LIVER DISEASES, AND THE USE THEREOF

(75) Inventors: Byung-Hoon Lee, Seoul (KR); Hu-Quan Yin, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 461 days.

(21) Appl. No.: 13/809,157

(22) PCT Filed: Jul. 15, 2011

(86) PCT No.: PCT/KR2011/005212
§ 371 (c)(1),
(2), (4) Date: Jan. 8, 2013

(87) PCT Pub. No.: WO2012/008788
PCT Pub. Date: Jan. 19, 2012

(65) Prior Publication Data
US 2013/0116321 A1 May 9, 2013

(30) Foreign Application Priority Data

Jul. 16, 2010 (KR) .................. 10-2010-0068784

(51) Int. Cl.
| | | |
|---|---|---|
| *A61K 31/198* | (2006.01) | |
| *A23L 2/52* | (2006.01) | |
| *A61K 9/00* | (2006.01) | |
| *A61K 47/02* | (2006.01) | |
| *A61K 47/26* | (2006.01) | |
| *A61K 9/20* | (2006.01) | |
| *A61K 9/48* | (2006.01) | |

(52) U.S. Cl.
CPC ............. *A61K 31/198* (2013.01); *A23L 2/52* (2013.01); *A23L 33/15* (2016.08); *A23L 33/16* (2016.08); *A23L 33/175* (2016.08); *A61K 9/0019* (2013.01); *A61K 9/2018* (2013.01); *A61K 9/2059* (2013.01); *A61K 9/4858* (2013.01); *A61K 9/4866* (2013.01); *A61K 47/02* (2013.01); *A61K 47/26* (2013.01)

(58) Field of Classification Search
USPC ........................................................ 514/561
See application file for complete search history.

(56) References Cited

U.S. PATENT DOCUMENTS

| | | | | |
|---|---|---|---|---|
| 6,048,543 | A * | 4/2000 | Schneider et al. | 424/442 |
| 6,620,967 | B1 * | 9/2003 | Kobayashi | 562/433 |
| 2004/0192751 | A1 * | 9/2004 | Abe et al. | 514/400 |

FOREIGN PATENT DOCUMENTS

| | | | |
|---|---|---|---|
| KR | 10-1998-0702436 A | | 7/1998 |
| KR | 1019980702436 | * | 7/1998 |
| KR | 10-2004-0094749 A | | 11/2004 |
| KR | 10-0969170 B1 | | 7/2010 |

OTHER PUBLICATIONS

Patient.co uk. Steatohepatitis and Steatosis (Fatty liver). Retrieved from the Internet, [Retrieved on Apr. 11, 2015], <URL: http://www.patient.co.uk/doctor/steatohepatitis-and-steatosis-fatty-liver>.*
PubChem CID 5951. L-Serine. Retrieved from the Internet, [Retrieved on Apr. 11, 2015], <URL:https://pubchem.ncbi.nlm.nih.gov/compound/L-serine>.*
Rubin et al. Fatty Liver, Alcoholic Hepatitis and Cirrhosis Produced by Alcohol in Primates. N Engl J Med (1974), vol. 290, pp. 128-135.*
Yahagi et al. Absence of Sterol Regulatory Element-binding Protein-1 (SREBP-1) Ameliorates Fatty Livers but Not Obesity or Insulin Resistance in Lepob/Lepob Mice. The Journal of Biological Chemistry (2002) vol. 277 pp. 19353-19357.*
Laura E.Nagy:Molecular Aspects of Alcoholmetabolism:Transcription Factors Involved in Early Ethanol-Induced Liver Injury, Annu. Rev.Nutr.2004. 24:55-78.
Janardan K.Reddy: Nonalcoholic Steatosis and Steatohepatitis III. Peroxisomal beta-oxidation, PPARα, and steatohepatitis, Am.J.Physiol.Gastrointest.Liver Physiol, 281:G1333-1339, 2001.
Fischer M et al., Peroxisome Proliferator-activated Receptor α (PPARα) Agnoist Treatment Reverse PPARα Dysfunction and Abnormalities in Hepatic Lipid Metabolism in Ethanol-fed Mice, J.Biol.Chem. vol. 278, No. 30, Issue of Jul. 25, pp. 27997-28004, 2003.
Cheng Ji et al., Predominant role of sterol response element binding proteins (SREBP) lipogenic pathways in hepatic steatosis in the murine intragastric ethanol feeding model, Journal of Hepatology 45:717-724, 2006.
Yin Hu-Quan et al., Honokiol reverses alcoholic fatty liver by inhibiting the maturation of sterol regulatory element binding protein-1c and the expression of its downstream lipogenesis genes, Toxicology and Applied Pharmacology 236:124-130, 2009.
Song Zhenyuan et al., S-Adenosylmethionine (SAMe) protects against acute alcohol induced hepatotoxicity in mice, J Nutr. Biochem. 14: 591-597, 2003.
Yin Hu-Quan et al., Magnolia officinalis Reverses Alcoholic Fatty Liver by Inhibitting the Maturation of Sterol Regulatory Element-Binding Protein-1c, J Pharmacol Sci 109, 486-495, 2009.
Lee Hee Sun et al., Effects of Chlorella vulgaris on lipid metabolism in Wistar rats fed high fat diet, Nutrition Research and Practice 2(4), 204-210, 2008.

* cited by examiner

*Primary Examiner* — Kendra D Carter
*Assistant Examiner* — Taina D Matos Negron
(74) *Attorney, Agent, or Firm* — Vorys, Sater, Seymour & Pease LLP; Mih Suhn Koh

(57) ABSTRACT

The present invention is related to a composition comprising a serine as an active ingredient for treating or preventing fatty liver diseases. The inventive compound significantly inhibits the SREBP-1 transcription activity involved in lipid synthesis and reduced the fatty liver formation through various in vitro test and in vivo test therefore it can be useful in the prevention and treatment of the fatty liver diseases as a medicament or health functional food.

3 Claims, 4 Drawing Sheets

COMPOSITION CONTAINING SERINE AS AN ACTIVE INGREDIENT FOR THE PREVENTION AND TREATMENT OF FATTY LIVER DISEASES, AND THE USE THEREOF

TECHNICAL FIELD

The present invention is related to a composition for the prevention and treatment of fatty liver diseases containing serine as an active ingredient and the use thereof.

BACKGROUND ART

The mortal rate caused by liver disease in Korea has reached to very high level, i.e., about 23.5 per 100000 (male: 37.8, female: 9.0), which is principle pathology resulting in death of middle-aged Korean. Especially, an alcoholic liver disease is mainly caused by chronic over-drinking. The alcoholic liver diseases include fatty liver, chronic hepatitis, acute hepatitis, liver cirrhosis, and liver cancer, especially, the alcoholic fatty liver is a mild and early-stage liver disease induced by excess consumption of ethanol. Because it was generally considered to be benign and reversible, there is no standard method for the treatment of the disease. However, it is now being recognized that fatty liver, if not treated properly, leads to steatohepatitis, fibrosis and ultimately end-stage liver disease.

The etiology of alcoholic liver disease has not yet fully identified till now. Alcohol affects on the transcription activity of various transcription factors, which has been reported to cause to the metabolic disorder of fatty acid. Specifically, various genes involved in lipid oxidation are controlled by particular transcription factors, especially, PPAR-alpha involved in lipid oxidation and SREBP-1 (sterol response element binding protein 1) involved in lipogenesis (Laura E. Nagy: Molecular aspects of alcohol metabolism; Transcription factors involved in early ethanol-induced liver injury, *Annu. Rev. Nutr.* 24:55-78, 2004). PPAR-alpha plays important roles in lipid oxidation in liver and forms complex-dimer with RXR-alpha when it is activated by ligands, resulting in inducing the expression of various genes (Reddy JK: Nonalcoholic steatosis and steatohepatitis. II. Peroxisomal beta-oxidation, PPAR-alpha and steatohepatitis, *AM. J. Physiol. Gastrointest. Liver Physiol.*, 281:G1333-29, 2001). However, alcohol inhibits the activity of transcription factors such as PPAR-alpha and then inhibits the lipolysis resulting in the formation of fatty liver. Therefore, the increase of the PPAR-alpha activity increases lipid oxidation and prevents from the formation of fatty liver. For example, 4-week's administration of alcohol into mice decreased the transcription activity of PPAR-alpha resulting in the formation of fatty liver however the co-treatment with PPAR-alpha activator did not form the fatty liver (Fisher M et al., Peroxisome proliferator-activated receptor agonist treatment reverse PPAR-alpha dysfunction and abnormalities in hepatic lipid metabolism in ethanol-fed mice, *J. Biol., Chem.,* 278, pp. 27997-8004, 2004).

SREBP-1 (sterol response element binding protein 1) is a crucial factor controlling the several gens involved in tri-glyceride formation and the increased activity of the transcription of SREBP-1 stimulated the lipogenesis resulting in fatty liver. Alcohol increases the expression of SREBP-1, which causes the various genes involved in lipid biosynthesis resulting in the increase of lipid synthesis. Accordingly, the decrease of SPEBP-1 expression could prevent from the formation of fatty liver. For example, it has been observed that the fatty liver induced by alcohol feeding was signifi- cantly reduced in the transgenic mouse defected with SREBP-1 expression (Cheng Ji et al; Predominant role of sterol response element binding proteins (SREBP) lipogenic pathways in hepatic steatosis in the murine intragastric ethanol feeding model, *Journal of Hepatology,* 45:717-724, 2006).

Accordingly, the increase of transcription activity of PPAR-alpha controlling the synthesis of enzyme involved in lipid oxidation and inhibition of transcription activity of SREBP-1 involved in lipogenesis could efficiently prevent from the alcoholic fatty liver.

However, there has been not reported or disclosed about the therapeutic effect of serine on liver diseases in any of above cited literatures, the disclosures of which are incorporated herein by reference.

Therefore, the present inventors have endeavored to find the effective agent for treating liver diseases and found that the serine inhibits the SREBP-1 transcription activity involved in lipid synthesis and reduced the fatty liver formation through various in vitro test such as the inhibition effect on lipid accumulation caused by alcohol in H4IIEC3 cell as well as inhibition effect on SREBP1 activation and in vivo test such as the inhibition effect on the fatty liver formation, triglyceride accumulation, lipid metabolism indicators, ALT activity, and triglyceride level in acute and chronic fatty liver induced mouse model fed by alcohol.

SUMMARY OF THE INVENTION

According to one aspect, the present invention also provides a use of serine for the manufacture of medicament employed for treating or preventing fatty liver diseases in human or mammal.

The present invention also provides a method for treating fatty liver diseases in human or mammal comprising administering to said mammal an effective amount of above-mentioned serine, together with a pharmaceutically acceptable carrier thereof.

The present invention provides a pharmaceutical composition comprising serine as an active ingredient for treating or preventing fatty liver diseases.

The present invention also provides a health functional food comprising the above-described serine for the prevention or improvement of fatty liver disease as an active ingredient in an amount effective to preventing and improving fatty liver diseases, together with a sitologically acceptable additive.

DETAILED DESCRIPTION OF THE INVENTION

Accordingly, it is an object of the present invention to provide a pharmaceutical composition comprising serine as an active ingredient for treating or preventing fatty liver diseases, together with a pharmaceutically acceptable carrier.

It is another object of the present invention to provide a use of serine for the manufacture of medicament employed for treating or preventing fatty liver diseases in human or mammal.

It is the other object of the present invention to provide a method for treating fatty liver diseases in human or mammal comprising administering to said mammal an effective amount of serine, together with a pharmaceutically acceptable carrier thereof.

The term "serine" disclosed herein comprise the compound itself, the pharmaceutically acceptable salt or the solvates thereof as well as the stereoisomer, i.e., L-serine and D-serine, preferably, L-serine represented by chemical formula 1:

[Chemical formulae 1]

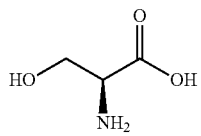

In accordance with one aspect of the present invention, there provided a health functional food comprising a serine, the pharmaceutically acceptable salt or the solvates thereof for the prevention or improvement of liver diseases an active ingredient in an amount effective to prevent and improve fatty liver diseases, together with a sitologically acceptable additive.

The term "pharmaceutical composition" disclosed herein is characterized that the serine inhibits the SREBP-1 transcription activity of which enzyme regulates the synthesis of lipogenesis-involved enzyme.

The term "fatty liver diseases" disclosed herein comprises acute or chronic alcoholic fatty liver, acute or chronic non-alcoholic fatty liver, nutritional fatty liver, starvation fatty liver, obese fatty liver, diabetic fatty liver, cholestatic hepatitis, acute or chronic cholestatic liver disease, preferably, acute or chronic alcoholic fatty liver or acute or chronic non-alcoholic fatty liver, more preferably, acute or chronic alcoholic fatty liver.

The pharmaceutical composition for treating liver diseases could contain about 0.01 to 95 w/w %, preferably 0.5 to 50 w/w % of inventive extract or compound of present invention based on the total weight of the composition.

An inventive compound may be procured from conventionally available company.

The inventive compound can be transformed into their pharmaceutically acceptable salt and solvates by the conventional method well known in the art. For the salts, acid-addition salt thereof formed by a pharmaceutically acceptable free acid thereof is useful and can be prepared by the conventional method. For example, after dissolving the compound in the excess amount of acid solution, the salts are precipitated by the water-miscible organic solvent such as methanol, ethanol, acetone or acetonitrile to prepare acid addition salt thereof and further the mixture of equivalent amount of compound and diluted acid with water or alcohol such as glycol monomethylether, can be heated and subsequently dried by evaporation or filtrated under reduced pressure to obtain dried salt form thereof.

As a free acid of above-described method, organic acid or inorganic acid can be used. For example, organic acid such as methansulfonic acid, p-toluensulfonic acid, acetic acid, trifluoroacetic acid, citric acid, maleic acid, succinic acid, oxalic acid, benzoic acid, lactic acid, glycolic acid, gluconic acid, galacturonic acid, glutamic acid, glutaric acid, glucuronicacid, aspartic acid, ascorbic acid, carbonylic acid, vanillic acid, hydroiodic acid and the like, and inorganic acid such as hydrochloric acid, phosphoric acid, sulfuric acid, nitric acid, tartaric acid and the like can be used herein.

Further, the pharmaceutically acceptable metal salt form of inventive compound may be prepared by using base. The alkali metal or alkali-earth metal salt thereof can be prepared by the conventional method, for example, after dissolving the compound in the excess amount of alkali metal hydroxide or alkali-earth metal hydroxide solution, the insoluble salts are filtered and remaining filtrate is subjected to evaporation and drying to obtain the metal salt thereof. As a metal salt of the present invention, sodium, potassium or calcium salt are pharmaceutically suitable and the corresponding silver salt can be prepared by reacting alkali metal salt or alkali-earth metal salt with suitable silver salt such as silver nitrate.

The pharmaceutically acceptable salt of the compound comprise all the acidic or basic salt which may be present at the compounds, if it does not indicated specifically herein. For example, the pharmaceutically acceptable salt of the present invention comprise the salt of hydroxyl group such as the sodium, calcium and potassium salt thereof; the salt of amino group such as the hydrogen bromide salt, sulfuric acid salt, hydrogen sulfuric acid salt, phosphate salt, hydrogen phosphate salt, dihydrophosphate salt, acetate salt, succinate salt, citrate salt, tartarate salt, lactate salt, mandelate salt, methanesulfonate(mesylate) salt and p-toluenesulfonate (tosylate) salt etc, which can be prepared by the conventional method well known in the art.

It is still another object of the present invention to provide a pharmaceutical composition comprising a serine, the pharmaceutically acceptable salt or the solvates thereof as an active ingredient for preventing and treating fattyliver diseases.

The inventive composition of the present invention significantly inhibits the SREBP-1 transcription activity involved in lipid synthesis and reduced the fatty liver formation through various in vitro test such as the inhibition effect on lipid accumulation caused by alcohol in H4IIEC3 cell as well as inhibition effect on SREBP1 activation and in vivo test such as the inhibition effect on the fatty liver formation, triglyceride accumulation, lipid metabolism indicators, ALT activity, and triglyceride level in acute and chronic fatty liver induced mouse model fed by alcohol.

The pharmaceutical composition for treating fatty liver diseases could contain about 0.01 to 99.9 w/w %, preferably 0.1 to 90 w/w % of the above crude drug composition of present invention based on the total weight of the composition.

The inventive composition may additionally comprise conventional carrier, adjuvants or diluents in accordance with a using method. It is preferable that said carrier is used as appropriate substance according to the usage and application method, but it is not limited. Appropriate diluents are listed in the written text of Remington's Pharmaceutical Science (Mack Publishing co, Easton Pa.).

Hereinafter, the following formulation methods and excipients are merely exemplary and in no way limit the invention.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinylpyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

Pharmaceutical formulations containing inventive composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), suppository, or sterile injectable preparation (solution, suspension, emulsion).

The inventive composition of the present invention in pharmaceutical dosage forms may be used in the form of their pharmaceutically acceptable salts, and also may be used alone or in appropriate association, as well as in combination with other pharmaceutically active compounds.

The desirable dose of the inventive composition varies depending on the condition and the weight of the subject, severity, drug form, route and period of administration, and may be chosen by those skilled in the art. However, in order to obtain desirable effects, it is generally recommended to administer at the amount ranging 0.01-10 g/kg, preferably, 1 to 5 g/kg by weight/day of the inventive composition of the present invention. The dose may be administered in a single or multiple doses per day. In terms of composition, the crude drug composition should be present between 0.01 to 80% by weight, preferably 0.5 to 50% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

In accordance with one aspect of the present invention, there provided a health functional food comprising a serine, the pharmaceutically acceptable salt or the solvates thereof for the prevention or improvement of fatty liver diseases as an active ingredient in an amount effective to preventing and improving fatty liver diseases, together with a sitologically acceptable additive.

The health functional food composition for preventing and improving fatty liver diseases could contain about 0.01 to 95 w/w %, preferably 0.5 to 80 w/w % of the above inventive composition of present invention based on the total weight of the composition.

Above described composition therein can be added to food, additive or beverage for prevention and improvement of fatty liver diseases. For the purpose of preventing and improving fatty liver diseases, wherein, the amount of above described crude drug composition in food or beverage may generally range from about 0.1 to 15 w/w %, preferably 1 to 10 w/w % of total weight of food for the health food composition and 1 to 30 g, preferably 3 to 10 g on the ratio of 100 ml of the health beverage composition.

Providing that the health beverage composition of present invention contains above described crude drug composition as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 ml of present beverage composition.

The other components than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition.

Examples of addable food comprising aforementioned crude drug composition therein are various food, beverage, gum, vitamin complex, health improving food and the like.

It will be apparent to those skilled in the art that various modifications and variations can be made in the compositions, use and preparations of the present invention without departing from the spirit or scope of the invention.

BRIEF DESCRIPTION OF THE DRAWINGS

The above and other objects, features and other advantages of the present invention will more clearly understood from the following detailed description taken in conjunction with the accompanying drawings, in which.

BEST MODE FOR CARRYING OUT THE INVENTION

The following Examples and Experimental Examples are intended to further illustrate the present invention without limiting its scope.

Reference Example 1

Sample Preparation

L-serine (S1315, Sigma Chemical Co. Ltd.) was procured and used in following experiment as a test sample

Example 1

Inhibition Effects of L-Serine on Ethanol Induced Lipid Accumulation in H4IIEC3

In order to investigate the inhibitory effect of the test sample on ethanol induced lipid accumulation in H4IIEc3, following experiment was performed according to the modified procedure disclosed in literature (Yin et al., Honokiol reverses alcoholic fatty liver by inhibiting the maturation of sterol regulatory element binding protein-1c and expression of its downstream lipogenesis genes: *Toxicol. Appl. Pharmacol.* 236:124-130, 2009).

1.1. H4IIEC 3 Cell Culture

H4IIEC 3 cell, a rodent liver cancer cell line, was procured from ATCC (American Type Culture Collection) and used in the experiment. The cell was cultured in RPMI1640 medium supplemented with 10% FBS, 100 U/ml of penicillin, 100 mg/ml of streptomycin at 37° C. in 5% $CO_2$ incubator and 1 ml of the cell was distributed to 96-well ($1 \times 10^4$/ml) to be stabilized until the cell had grown completely for 12-16 hours in 5% $CO_2$ incubator.

The cell was treated with ethanol or combination with ethanol with various concentration of L-serine (0.1 mM, 1 mM, and 10 mM) to incubate for 48 hrs.

1.2. Test Procedure

The cell was fixed with 4% paraformaldehyde and Nile red solution (1 mg/ml in DMSO) was added thereto to the extent that the final concentration had reached to 1 microgram/ml. The inhibition of lipid accumulation was determined by determining the fluorescence intensity of the Nil red changed by accumulated lipid induced by alcohol 5 mins after Nile red treatment through the observation with microscopy or microplate reader at 480 nm/580 nm.

Figure 1:
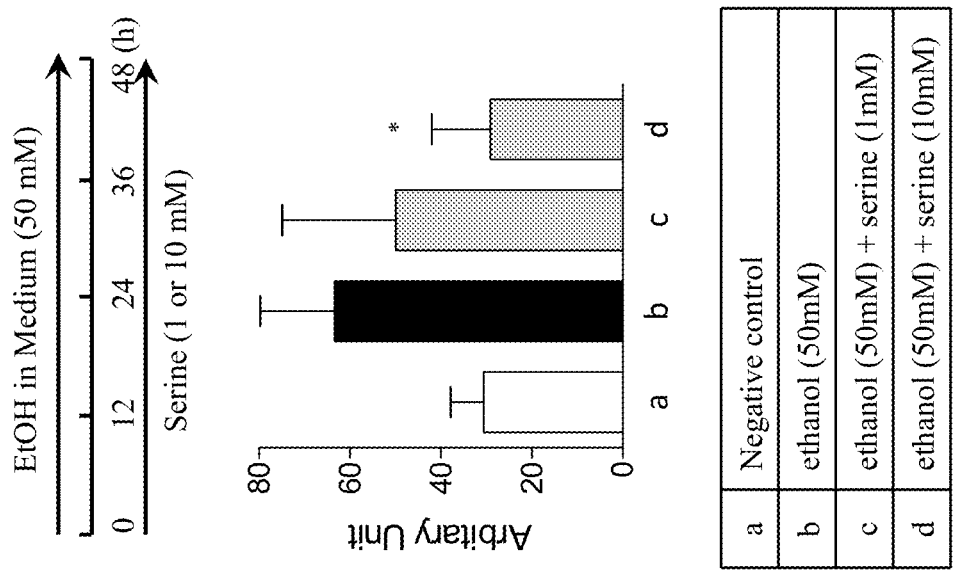
FIG. 1 shows the lipid accumulation in the test sample group treated with L-serine (Nile red staining)

At the result, the group treated with L-serine showed more decreased lipid accumulation than the group treatment with alcohol only and reduced fluorescence intensity to 29 unit than the ethanol control group (63.4 unit) ($P<0.05$) (See FIG. 1).

Example 2

Inhibition Effects of L-Serine on the Fatty Liver Formation in Acute Fatty Liver Induced Mouse Model Fed by Alcohol

In order to investigate the inhibitory effect on the formation of fatty liver in acute fatty liver induced mouse model fed with alcohol, following experiment was performed according to the modified procedure disclosed in literature (Song et al., S-Adenosylmethione protects against acute alcohol induced hepatotoxicity in mice, *J. Nutr. Biochem.* 14:591-597, 2003).

2.1. Experimental Animal

Male C57/BL mouse (19-21 g) procured from Central Lab. Animal Inc. (www.labanimal.co.kr) was bred according to GLP (Good Laboratory Practice) guideline in animal breeding room providing freely accessible water and solid feed, and acclimated with environment for 7 days before use. The breeding room was controlled by automatic light system from 8:00 A.M. to 8:00 P.M, for 12 hours with adjusting the temperature to 24° C. and the mouse was freely let to access to water and feed.

The mice were divided into four groups according to the dose of test samples and ethanol, i.e., (1) Group 1: Normal group which was not treated with any sample and was freely let to access to water and feed (2) Group 2: Ethanol treatment group which 50% ethanol in water was treated three times for every 12 hours (3) Group 3: low dose group which 20 mg/kg of L-serine was orally administrated twice, i.e., 30 mins after $2^{nd}$ treatment of ethanol and $3^{rd}$ treatment of ethanol, (4) Group 4: high dose group which 200 mg/kg of L-serine was orally administrated twice, i.e., 30 mins after $2^{nd}$ treatment of ethanol and $3^{rd}$ treatment of ethanol.

2.2. Experimental Procedure

Figure 2:
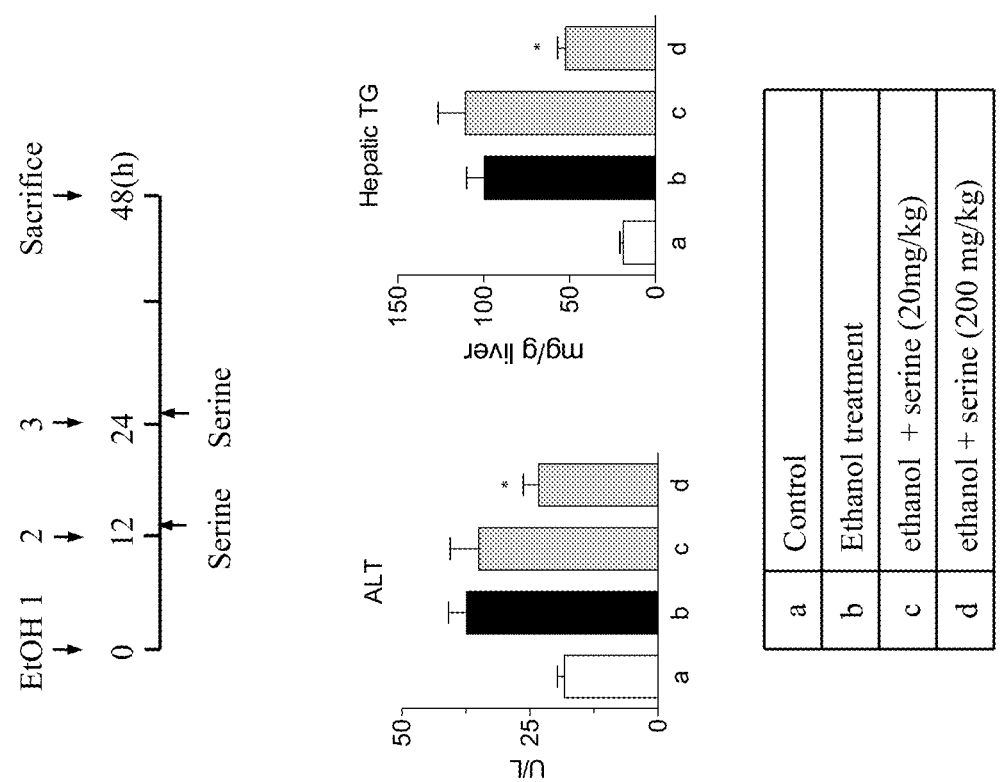
FIG. 2 represents the hepatic triglyceride level in the test sample group treated with L-serine in acute fatty liver induced mouse model fed by alcohol.

The collected blood from abdominal aorta in the rat was left alone for 1 hour at room temperature, centrifuged for 15 mins at 3000 rpm to afford serum and the serum was kept at −70° C. The ALT (s-GPT) enzyme activity was determined by analysis kit (YD diagnostics Inc, www.yd-diagnostics.com) according to the Reitman-Frankel method disclosed in preceding literature. The level of triglyceride in rat blood was determined by analysis kit analysis kit (Cat. No. TR0100, Sigma Aldrich Corp.) and the result was shown in FIG. 2.

At the result, it has been confirmed that the triglyceride level of the high dose group treated with 200 mg/kg of L-serine and ethanol was sharply reduced by 58.5% (52.4 mg/g) whereas that of ethanol treatment group was increased to 99.7 mg/g compared with normal group. (See FIG. 2).

Accordingly, it has been confirmed that L-serine has a potent treating activity in the treatment of acute alcoholic fatty liver disease.

Example 3

Effect on the Lipid Metabolism Indicators in Acute Fatty Liver Induced Mouse Model Fed by Alcohol

In order to confirm whether the anti-steatotic effects of L-serine on alcoholic fatty liver is caused by the inhibition of SREBP1 activity or not, following experiment was performed according to the modified procedure disclosed in literature (Yin et al., Magnolia officinalis reverses alcoholic fatty liver by inhibiting the maturation of sterol regulatory element binding protein-1c, *J. Pharmacol. Sci.* 109:486-495, 2009).

The expression of SREBP1 and its target gene product FAS were determined by the standard Western blot analysis using specific antibodies.

Figure 3:
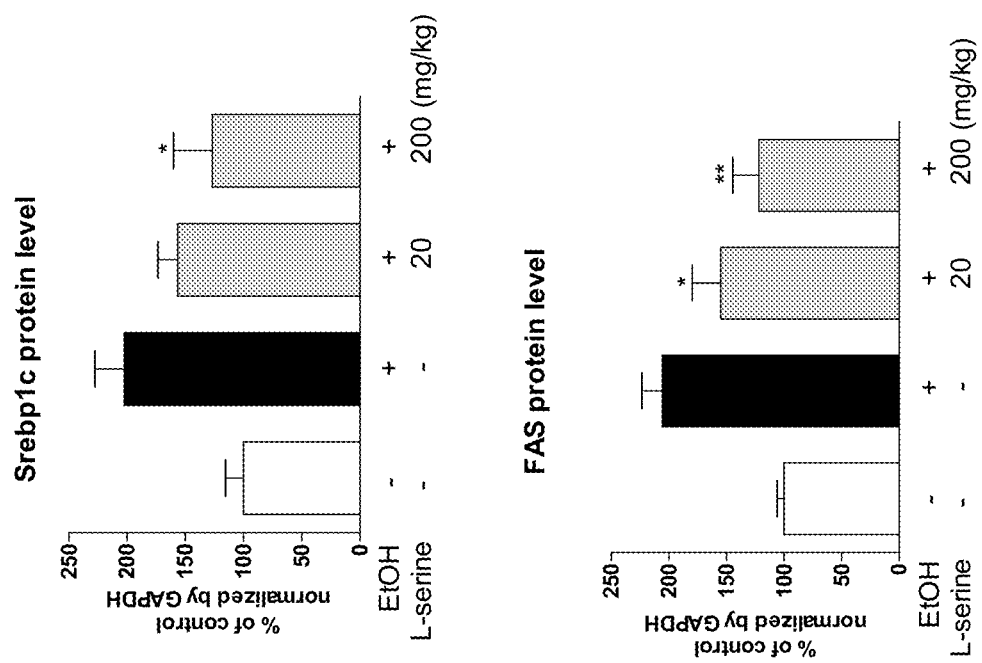
FIG. 3 shows the effect of L-serine on SREBP1 expression and FAS expression in acute fatty liver induced mouse model fed by alcohol.

At the result, it has confirmed that L-serine inhibited SREBP1 activation and FAS activation involved in lipogenesis and the result was shown in FIG. 3.

Accordingly, it has confirmed that L-serine has potent treating activity of alcoholic fatty liver disease, which is mediated by SREBP1.

Example 4

Inhibition Effects of L-Serine on the Hepatotoxicity and Fatty Liver in Chronic Ethanol Fed Rats

In order to investigate the effects of L-serine on the hepatotoxicity and fatty liver in chronic ethanol fed rats, ALT (s-GPT) enzyme activity in the serum and triglyceride level in the liver was determined according to the modified procedure disclosed in literature (Lee et al., Effect of *Chlorella vulgaris* on lipid metabolism in wistar rats fed high fat diet, *Nut. Pes. Prac.* 2:204-210, 2008).

4.1. Experimental Animal

Male wistar rat (170-190 g) procured from Central Lab. Animal Inc. (www.labanimal.co.kr) was bred according to GLP (Good Laboratory Practice) guideline in animal breeding room providing freely accessible water and solid feed, and acclimated with environment for 7 days before use. The breeding room was controlled by automatic light system from 8:00 A.M. to 8:00 P.M, for 12 hours with adjusting the temperature to 24° C. During the experiment, the rat was fed with liquid diet (Standard Lieber-Decarli, Dyets Inc, www.dyets.com) for providing appropriate calorie.

The rat were divided into five groups according to the dose of test samples and ethanol, i.e., (1) Group 1: Normal group which was treated with vehicle on the standard diet (Standard Lieber-Decarli control diet), (2) Group 2: Normal serine group which was treated with L-serine (1%) on the standard diet, (3) Group 3: Ethanol group which was treated with vehicle on the ethanol diet (Standard Lieber-Decarli ethanol diet) which comprises ethanol having 36% calorie among total calorie for 4 weeks, (4) Group 4: Ethanol-low L-serine group which was treated with 0.3% L-serine on the ethanol diet (Standard Lieber-Decarli ethanol diet) which comprises ethanol having 36% calorie among total calorie for 4 weeks, (5) Group 5: Ethanol-high L-serine group which was treated with 1% L-serine on the ethanol diet (Standard Lieber-Decarli ethanol diet) which comprises ethanol having 36% calorie among total calorie for 4 weeks.

4.2. Experimental Procedure

Figure 4:
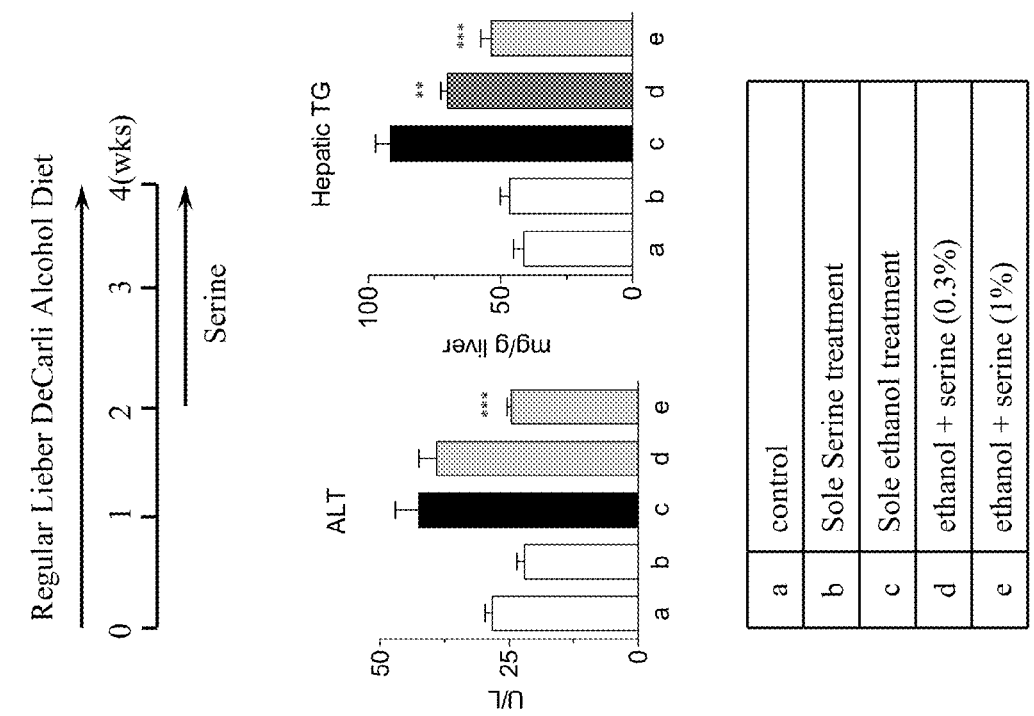
FIG. 4 represents the blood ALT level and hepatic triglyceride level in the test sample group treated with L-serine in chronic fatty liver induced mouse model fed by alcohol.

The collected blood from abdominal aorta in the rat was left alone for 1 hour at room temperature, centrifuged for 15 mins at 3000 rpm to afford serum and the serum was kept at −70° C. The ALT (s-GPT) enzyme activity was determined by analysis kit (YD diagnostics Inc, www.yd-diagnostics.com) according to the Reitman-Frankel method disclosed in preceding literature. The level of triglyceride in the rat liver was determined by analysis kit analysis kit (Cat. No. TR0100, Sigma Aldrich Corp.) and the result was shown in FIG. 4.

At the result, it has been confirmed that the test group treated with L-serine showed significantly reduced ALT enzyme activity (24.67 U/L) and hepatic triglyceride level (53.4 mg/g liver) whereas the ethanol treatment group showed increased ALT enzyme activity (42.5 U/L) and triglyceride level (91.69 mg/g liver). (See FIG. 4).

Accordingly, it has been confirmed that L-serine has a potent treating activity in the treatment of chronic alcoholic fatty liver disease.

Hereinafter, the formulating methods and kinds of excipients will be described, but the present invention is not limited to them. The representative preparation examples were described as follows.

| Preparation of powder | |
|---|---|
| L-serine | 25 mg |
| Corn Starch | 20 mg |
| Lactose | 30 mg |
| Mg stearate | optimum amount |

Powder preparation was prepared by mixing above components and filling sealed package.

| Preparation of tablet | |
|---|---|
| L-serine | 100 mg |
| Corn Starch | 10 mg |
| Lactose | 50 mg |
| Magnesium stearate | optimum amount |

Tablet preparation was prepared by mixing above components and entabletting.

| Preparation of capsule | |
|---|---|
| L-serine | 10 mg |
| Crystalline cellulose | 3 mg |
| Lactose | 14.8 mg |
| Magnesium stearate | 0.2 mg |

Tablet preparation was prepared by mixing above components and filling gelatin capsule by conventional gelatin preparation method.

| Preparation of injection | |
|---|---|
| L-serine | 10 mg |
| Mannitol | 180 mg |
| $Na_2HPO_4$—$12H_2O$ | 26 mg |
| Distilled water for injection | 1974 mg |

Injection preparation was prepared by dissolving active component, controlling pH to about 7.5 and then filling all the components in 2 ml ample and sterilizing by conventional injection preparation method.

| Preparation of liquid | |
|---|---|
| L-serine | 20 mg |
| Sugar | 20 g |
| Mannitol | 5 g |
| Distilled water | optimum amount |

Liquid preparation was prepared by dissolving active component, and then filling all the components in 1000 ml ample and sterilizing by conventional liquid preparation method.

| Preparation of health food | |
|---|---|
| L-serine | 1000 mg |
| Vitamin mixture | optimum amount |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Amide nicotinic acid | 1.7 mg |
| Folic acid | 50 μg |
| Calcium pantothenic acid | 0.5 mg |
| Mineral mixture | optimum amount |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

The above mentioned vitamin and mineral mixture may be varied in many ways. Such variations are not to be regarded as a departure from the spirit and scope of the present invention.

| Preparation of health beverage | |
|---|---|
| L-serine | 1000 mg |
| Vitamin C | 15 g |

-continued

| Preparation of health beverage | |
| --- | --- |
| Vitamin E(powder) | 100 g |
| Vitamin A | 0.2 g |
| Vitamin B$_1$ | 0.25 g |
| Vitamin B$_2$ | 0.3 g |
| Amide nicotinic acid | 3.5 g |
| Zinc oxide | 3.5 g |
| Ferrous lactate | 19.75 g |
| Distilled water | optimum amount |

Health beverage preparation was prepared by dissolving active component, mixing, stirred at 85° C. for 1 hour, filtered and then filling all the components in 1000 ml ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the inventive compound significantly inhibits the SREBP-1 transcription activity involved in lipid synthesis and reduced the fatty liver formation through various in vitro test such as the inhibition effect on lipid accumulation caused by alcohol in H4IIEC3 cell as well as inhibition effect on SREBP1 activation and in vivo test such as the inhibition effect on the fatty liver formation, triglyceride accumulation, lipid metabolism indicators, ALT activity, and triglyceride level in acute and chronic fatty liver model fed by alcohol.

The inventive compositions according to the present invention are useful in the prevention and treatment of the fatty liver diseases.

The invention claimed is:

1. A method of treating a fatty liver diseases in a subject having a symptom of a fatty liver disease from the increased SREB-1 transcription activity, comprising administering to the subject a pharmaceutical composition consisting of an effective amount of L-serine as an active ingredient, and a pharmaceutically acceptable carrier.

2. The method according to claim 1, wherein said fatty liver disease is selected from the group consisting of an acute or chronic alcoholic fatty liver, acute or chronic nonalcoholic fatty liver, acute cholestatic liver disease and chronic cholestatic liver disease.

3. A method of inhibiting the SREB-1 transcription activity of which the enzyme regulates the synthesis of lipogenesis-involved enzyme in a subject in need thereof, comprising administering to the subject a pharmaceutical composition consisting of an effective amount of L-serine as an active ingredient and a pharmaceutically acceptable carrier.

* * * * *